United States Patent [19]

Luukkainen et al.

[11] Patent Number: 4,578,076

[45] Date of Patent: Mar. 25, 1986

[54] MEDICATED INTRACERVICAL AND INTRAUTERINE DEVICES

[75] Inventors: Tapani Luukkainen, Helsinki; Ahti M. K. Liukkonen, Naantali, both of Finland

[73] Assignee: The Population Council, Inc., New York, N.Y.

[21] Appl. No.: 591,610

[22] Filed: Mar. 20, 1984

[51] Int. Cl.⁴ .................................................. A61F 5/46
[52] U.S. Cl. .................................. 604/892; 128/130; 128/131
[58] Field of Search ............... 604/891, 55, 54, 48, 604/60, 892; 128/127, 130, 131

[56] References Cited

U.S. PATENT DOCUMENTS

| | | | |
|---|---|---|---|
| Re. 30,312 | 6/1980 | Kessel | 128/130 |
| 3,467,089 | 9/1969 | Hasson | 128/130 |
| 3,889,666 | 6/1975 | Lerner | 128/127 |
| 3,935,860 | 2/1976 | Hoff | 604/55 |
| 4,341,728 | 7/1982 | Robertson et al. | 264/161 |
| 4,480,642 | 11/1984 | Stoy et al. | 128/130 |

FOREIGN PATENT DOCUMENTS 2826352  12/1979  Fed. Rep. of Germany ...... 128/130

Primary Examiner—C. Fred Rosenbaum
Assistant Examiner—Sherri E. Vinyard
Attorney, Agent, or Firm—Brumbaugh, Graves, Donohue & Raymond

[57] ABSTRACT

This invention relates to a medicated device for insertion into the uterus or cervix comprising a T-shaped platform and a drug release attachment thereon, the platform having a vertical stem portion with a rounded knob portion at the top thereof and two flat flexible downwardly slanting arms extending from the knob, the arms tapering to a lesser dimension at the end from the knob to the end of the arms and the arms having a downward bend of about 45°–110° proximate the end of each arm.

8 Claims, 2 Drawing Figures

MEDICATED INTRACERVICAL AND INTRAUTERINE DEVICES

BACKGROUND OF THE INVENTION

A variety of chemical and mechanical methods for controlling fertility and for preventing pregnancy are known. Approaches such as sterilization, the use of condoms, intrauterine devices (herein "IUD"), intracervical devices, (herein "ICD"), spermicidal creams and jellies, foam tablets, and oral pills are currently available to prevent pregnancy. These methods, though effective to a variable extent, also have limitations. Most of these devices require constant motivation on the part of the user and some approaches such as sterilization, ICDs and IUDs require specialized medical attention.

Oral contraceptives are a popular method of contraception, but have many undesirable side effects and require the daily ingestion of a tablet. The use of a medicated intracervical or intrauterine device as a means of administering effective contraceptive steroids through a vaginal or uterine route is seen as a means of overcoming some of these drawbacks.

It is known that intrauterine devices can provide a system for timed release, local administration of a drug. For example, IUDs having a drug-releasing erodible outer layer or partial covering have been suggested as a means for delivering drugs to the uterus. In one example of the foregoing, it has been suggested that a small section of a Lippes loop be coated with an erodible polymer containing an appropriate drug. In another example, a sleeve of bioerodible material, having a contraction inducing drug distributed therein, is attached to an IUD that is especially constructed to deteriorate and be ultimately expelled from the uterus after use.

U.S. Pat. No. 4,341,728 to Robertson, et al. describes a particularly useful medicated IUD. According to that invention, an intrauterine controlled release drug delivery article is associated with a proven IUD platform. The drug release article is constructed for attachment to a known platform, which is nonmedicated and relatively stable. The drug release article can be for example a molded sleeve tightly secured on a stem of an extant IUD.

In the Robertson et al. invention, an outer drug permeable tube surrounds the drug release sleeve, thus controlling the rate of administration of the drug contained in the drug release sleeve. RTV silicone rubbers are employed as the base or carrier material of the sleeve in the IUD disclosed by Robertson et al. Removal of the fillers from commercially available silicone rubber, for example by centrifuging, makes the silicone rubber used by Robertson et al. more satisfactory for drug release. The use of the outer drug permeable tube which fits tightly over the drug release sleeve also imparts structural integrity to the fillerless silicone rubber of the sleeve which permits it to be easily handled without deterioration prior to insertion in the uterus.

Medicated IUDs as described in U.S. Pat. No. 4,341,728 are useful but have several drawbacks. An IUD is designed to be inserted into the woman's uterus which makes positioning of the IUD important and requires insertion and removal by a qualified health professional. Known IUDs are also often associated with undesirable bleeding of the endometrium lining due to irritation.

Medicated intracervical devices (ICDs) which are introduced into the cervical canal just beyond the cervical os in order to prevent pregnancy are also known and have also been used to release contraceptive hormones i.e., El Mahgoub, S., *Contraception,* 1982, Vol. 25, No. 4, p. 357–374. Like medicated IUDs. Medicated ICDs can be useful for the inhibition of fertility but are also useful in treating and medicating other conditions of the female reproductive system.

SUMMARY OF THE INVENTION

Easy to insert medicated ICDs and IUDs which reduce the bleeding of the endometrium associated with conventional IUDs and which provide long term intracervical and intrauterine drug release have now been found. The novel medicated IUD/ICD comprises an existing drug release attachment attached to a T-shaped platform having a vertical stem portion with a rounded knob at the top of the vertical stem and two flat flexible downward slanting arms extending from the knob, the arms tapering from the knob to the ends of the arms and having a downward bend of about 45°–110° proximate the end of each arm. The drug release attachment can be a molded sleeve which is tightly secured on the stem of the ICD or IUD as described in U.S. Pat. No. 4,341,728 which is incorporated herein by reference. The ICD and IUD are of the same design but have different dimensions.

DESCRIPTION OF PREFERRED EMBODIMENT

Figure 1:
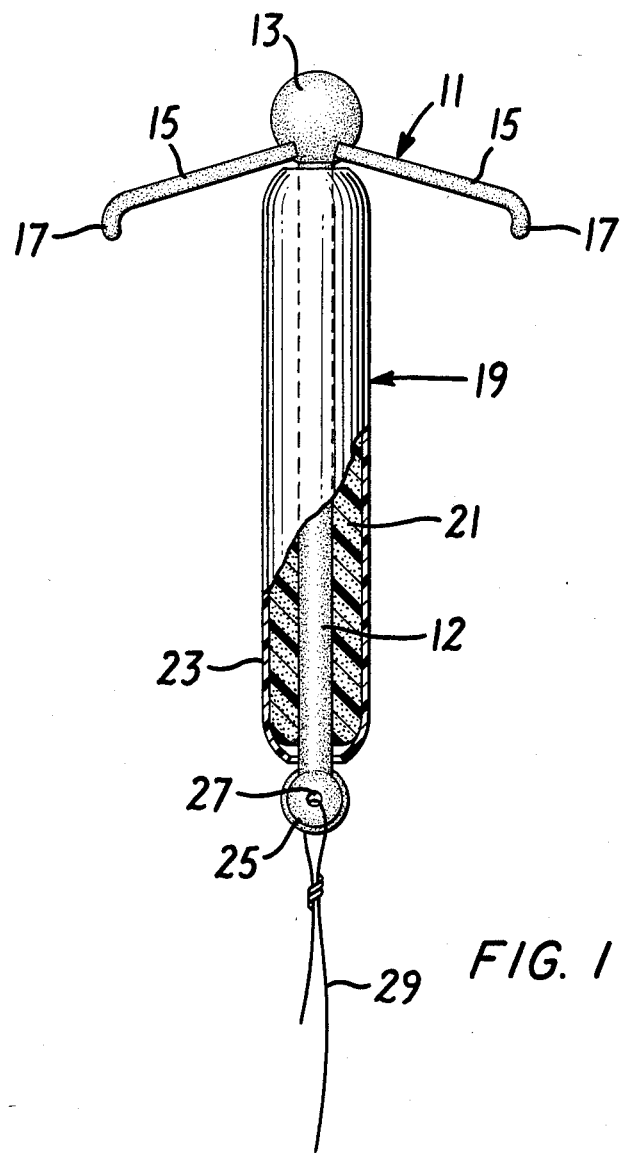
FIG. 1 is an enlarged plan view, partially in section, and illustrates the platform carrying a drug-release attachment.
Figure 2:
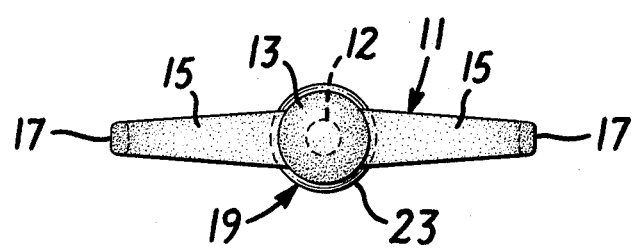
FIG. 2 is a top view of the platform.

As illustrated in FIG. 1, both the medicated ICD or IUD comprises a T-shaped platform 11 including a vertical stem portion 12 which has a rounded knob 13 at the top of the stem and flexible downward slanting arms 15 extending from the knob 13. The arms 15 taper from the knob to the ends of the arms and have a downward bend 17 of about 45°–110° proximate the end of the arms.

Preferably the angle is about 90° and is located at a distance about 2 mm–8 mm from the end of the arms. The flexible arms 15 serve to anchor the ICD or IUD in place so that it will not be expelled from the internal os of the cervix or from the uterus once it is inserted. The arms 15 slant down from the knob 13 at an angle of about 10°–25°.

The stem 12 supports a drug release attachment The attachment, can be for example, a sleeve 21 of a carrier or base material such as silicone rubber with a suitable drug evenly distributed throughout as described in U.S. Pat. No. 4,341,728.

In the drug release attachment, sleeve 21, one can employ any agent or drug used to treat the cervix or uterus or for controlling fertility. Suitable agents for use in the IUD and ICD include, without limitation, drugs that produce a physiologically or pharmacologically localized or systemic effect, and a contraceptive effect in animals, including domestic warm blooded mammals, human and primates, valuable domestic household, sport or farm animals such as horses, dogs, cats, cattle, sheep and the like; or for administering to laboratory animals such as mice, monkeys, rats, rabbits and guinea pigs. The active drugs that can be administered by the novel IUD and ICD include, without limitation: anti-fertility agents, which broadly includes progestational substances, estrogenic substances and mixtures thereof, that have anti-fertility properties. These substances can be of naturally occurring or synthetic origin and they generally possess a cyclopentanophenanthrene nucleus. The term progestational substance as used herein embraces "progestogen" which term is used in the steroid art to generically describe sterioids possessing progestational activity, and the former also includes "progestins", a term widely used for synthetic sterioids that have progesteroid effects. The active anti-fertility agent that can be used to produce the desired effects in female mammals, including humans and primates that are able to maintain control of the reproduction process, include without limitations: pregn-4-ene-3,20-dione (also known as progesterone); 19-nor-pregn-4-ene-3,20-dione; 17-hydroxy-19-nor-17α-pregn-5(10)-ene-20-yn-3-one; dl-11β-ethyl-17-ethinyl-17-β-hydroxygon-4-ene-3-one; 17α-ethinyl-17-hydroxy-5(10)-estren-3-one; 17α-ethinyl-19-norestosterone; 6-chloro-17-hydroxypregna-4,6-diene-3,20-dione; 17β-hydroxy-6α-methyl-17-(1-propynyl)androst-4-ene-3-one; 9β,10α-pregna-4,6-diene-3,20-dione; 17-hydroxy-17α-pregn-4-en-20-yne-3-one; 19-nor-17α-pregn-4-en-20-yne-3β,17-diol; 17-hydroxypregn-4-ene-3,20-diene; 17-hydroxy-6α-methylpregn-4-ene-3,20-dione; 17-hydroxy-pregn-4-ene-3,20-dione; 17-α-hydroxyprogesterone; mixtures thereof and the like.

The term estrogenic and estrogenic anti-fertility agents as used herein also includes the compounds known as estrogens, and the metabolic products thereof that possess anti-fertility properties or are converted to active anti-fertility agents in the uterus or cervix. Exemplary estrogenic compounds include β-estradiol, β-estradiol 3-benzoate, 17-β-cyclopentanepionate estradiol, 1,3,5(10-estratnene-3,17β-diol dipropionate, estra-1,3,5(10-triene-3,17-β-diolvalerate, estrone, ethinyl estradiol, 17-ethinyl estradiol-3 methyl ether, 17-ethinyl estradiol-3-cyclopentoether, estriol, mixtures thereof, and the like.

Additional agents or drugs that can be delivered by the IUD and ICD include antibiotics such as tetracycline; anti-bacterials such as sulfonamides; anti-inflammatories such as dexamethasone; hormonal agents such as prostaglandin $F_2$; and the like.

Overlying the sleeve 21, a length of drug permeable tubing 23 tightly fits about the sleeve and controls the rate of administration of the drug contained in the attachment. RTV silicone rubbers can be employed as the base or carrier material of the attachment. Removal of the fillers from commercially available silicone rubber, for example by centrifuging, makes the silicone rubber more satisfactory for drug release. The use of the outer drug permeable tube 23 which fits tightly over the sleeve 21 imparts structural integrity to the fillerless silicone rubber of the sleeve in order to permit the ICD or IUD to be handled in an ordinary way prior to insertion.

Unlike the medicated IUD described in U.S. Pat. No. 4,341,728 the novel medicated ICD or IUD described herein is easily inserted just beyond the cervical os or into the uterus and does not require the assistance of a health professional. IUDs and ICDs are normally inserted and positioned using a hollow flexible plastic inserter tube. The arms of this novel ICD/IUD are very flexible and unlike known ICDs and IUDs the arms need not be placed inside the inserter tube in order to be properly positioned in the cervical canal or uterus. Only the stem portion of the platform need be placed inside the inserter tube and the flexible arms may remain outside.

The knob at the top of the IUD/ICD stem serves to open the cervix as the inserter tube is introduced into the vaginal canal. The knob also protects the walls of the vaginal canal and the cervix from injury by the leading edge of the inserter tube. The stem is placed in the inserter tube with the flexible arms extending outward over the top of the inserter. As the inserter is introduced into the vaginal canal the flexible arms fold down against the inserter tube and the knob serves to open the canal as the ICD/IUD is pushed into position. The tapered shape and bent ends of the arms prevent them from twisting as the IUD/ICD is positioned in the cervical canal or uterus. The upward pressure of the flexible arms against the cervix or uterus wall holds the IUD/ICD in place. Once inserted, the medicated IUD/ICD can be left in place for up to eight years.

The arms of known IUDs and ICDs for example as described in U.S. Pat. No. 4,341,728 are too long and too inflexible to be inserted and positioned in this manner. Conventional ICDs and IUDs must be inserted with the arms inside the inserter tube and therefore require the use of a rod to push the IUD or ICD out of the inserter tube after it is in place in the patient's uterus or cervix.

Both the IUD/ICD platform and the drug releasing sleeve can be made as described in U.S. Pat. No. 4,341,728. This one piece molded construction provides a safe IUD/ICD which will not separate or break into pieces during use.

The dimensions of the ICD and IUD can vary in a range of about 10% but generally they will be as follows:

| ICD | |
|---|---|
| Vertical stem (12) | |
| length | 20.0 mm |
| diameter | 1.2 mm |
| Top rounded knob diameter (13) | 3.0 mm |
| Arms (15) | |
| length to bend (17) | 6.0 mm |
| width | 0.4 mm |
| length from bend to end | 0.5 mm |
| IUD | |
| Vertical stem (12) | |
| length | 26.0 mm |
| diameter | 1.4 mm |
| Top rounded knot diameter (13) | 3.4 mm |
| Arms (15) | |
| length to bend (17) | 14.0 mm |
| width | 1.0 mm |
| length from bend to end | 1.0 mm |

In another preferred embodiment, the stem 12 is equipped with means for removing the IUD/ICD from the cervix or uterus for example, a small knob 25 on the bottom end. This knob also helps to hold the medicated sleeve in place on the stem and is about 2.0 mm in diameter. The knob has a hole 27 through which a thread 29 is attached for use in removing the ICD or IUD. The stem can alternately be fitted with a loop through which the thread can be attached.

I claim:

1. A medicated device for retention in the cervix comprising a T-shaped platform, the platform having a vertical stem portion with a drug release attachment thereon, a rounded knob portion at the top thereof and two flat flexible downwardly slanting arms extending from the knob, the arms tapering to a lesser dimension from the knob to the end of the arms, and the ends of the arms having a downward bend of about 45°–110°, said vertical stem being about 18–22 mm in length, and said arms measuring about 5–7 mm from the knob to the downward bend.

2. The medicated intracervical device as described in claim 1, wherein the drug release attachment tightly secured on the stem portion of the platform comprises a molded sleeve containing a drug which can be delivered through the cervix.

3. The medicated intracervical device as described in claim 2, wherein the molded sleeve is fitted with a length of drug permeable tubing.

4. The medicated intracervical device as described in claim 1, wherein the stem has a means for removing the device attached to the bottom end.

5. The medicated intracervical device as described in claim 2 wherein the downward bend is at an angle of about 90° and is located about 0.5 mm from the end of each arm.

6. A device for retention in the cervix comprising a T-shaped platform having a vertical stem portion with a rounded knob portion at the top thereof and two flat flexible downwardly slanting arms extending from the knob, the arms tapering to a lesser dimension from the knob to the end of the arms, and the ends of the arms having a downward bend of about 45°–110°, said vertical stem being about 18–22 mm in length, and said arms measuring about 5–7 mm from the knob to the downward bend.

7. The intracervical device as described in claim 6, wherein the stem has a means for removing the device attached to the bottom end.

8. The intracervical device as described in claim 6 wherein the downward bend is at an angle of about 90° and is located about 0.5 mm from the end of each arm.

* * * * *

UNITED STATES PATENT AND TRADEMARK OFFICE
CERTIFICATE OF CORRECTION

PATENT NO. : 4,578,076
DATED : March 25, 1986
INVENTOR(S) : Luukkainen et al.

It is certified that error appears in the above-indentified patent and that said Letters Patent is hereby corrected as shown below:

Column 1, line 6, after "BACKGROUND OF THE INVENTION", insert --This invention was made with funds from the U.S. government, which has certain rights in the invention.--.

Signed and Sealed this

Twenty-fourth Day of September, 1996

Attest:

BRUCE LEHMAN

*Attesting Officer*    *Commissioner of Patents and Trademarks*